United States Patent [19]

Murao et al.

[11] Patent Number: 5,169,778
[45] Date of Patent: Dec. 8, 1992

[54] AMYCOLATOPSIS TREHALOSTATICA STRAIN

[75] Inventors: Sawao Murao, Sakai; Takashi Shin, Sanda, both of Japan

[73] Assignee: Sawao Murao, Osaka, Japan

[21] Appl. No.: 601,738

[22] PCT Filed: Feb. 28, 1990

[86] PCT No.: PCT/JP90/00264
§ 371 Date: Dec. 6, 1990
§ 102(e) Date: Dec. 6, 1990

[87] PCT Pub. No.: WO90/10010
PCT Pub. Date: Sep. 7, 1990

[30] Foreign Application Priority Data

Feb. 28, 1990 [JP] Japan .................. 1-45394

[51] Int. Cl.$^5$ .............................................. C12N 1/14
[52] U.S. Cl. ................................. 435/254; 435/911
[58] Field of Search ............................ 435/254, 911

[56] References Cited

U.S. PATENT DOCUMENTS

4,920,215  4/1990  Holdom et al. ........................ 435/872
4,981,799  1/1991  Takahashi et al. .................... 435/233

FOREIGN PATENT DOCUMENTS

A1544068  4/1977  United Kingdom ............... 407/14

OTHER PUBLICATIONS

Gordon et al., *Int. J. of Syst. Bact.*, vol. 24(1), 1974, pp. 54–63.
Ezaki et al., Int. J. of Syst. Bact., vol. 39(3), 1989, pp. 224–229.
Sneath et al., *Bergey's Manual of Systematic Bact.*, vol. 2, pp. 1465, 1469, 1470, 1495 and 4500.
Gherna et al., ATCC, *Catalogue of Bacteria and Phages*, 17th ed., p. 16.
The Journal of Antibiotics, vol. 41, No. 10, pp. 1506–1510 (1988).
The Journal of Antibiotics, vol. 41, No. 11, pp. 1525–1532 (1988).
Biochemical and Biophysical Research Communications, vol. 77, No. 2, pp. 449–456 (1977).
Chemical Abstracts, vol. 111, No. 21, p. 331, ab. No. 190010 j (1989).
The Journal of Antibiotics, vol. XL, No. 4, pp. 563–565 (1987).

*Primary Examiner*—Johnnie R. Brown
*Assistant Examiner*—Pamela S. Webber
*Attorney, Agent, or Firm*—David G. Conlin; Ernest V. Linek

[57] ABSTRACT

This invention relates to a substance Trehalostatin which is a white powder soluble in water but hardly or only slightly soluble in hexane, benzene, ethers and petroleum ether, shows no absorption maxima at 220 nm or above in its ultraviolet visible light absorption spectrum, is positive in Rydon-Smith reaction and negative in ninhydrin reaction, 3,6-dinitrophthalic acid reaction and Elson-Morgan reaction, has an Rf value of 0.37 in Merk Kieselgal 60 $G_{254}$ thin layer chromatography using a 3:1:2 mixture of n-butanol, acetic acid and water as a developing solvent, and Rt of 11.0 minutes in YMC PA03 (0.7×27 cm) high performance liquid chromatography using 65% v/v acetonitrile (in $H_2O$) as a solvent at a flow rate of 1.0 ml/min, has a molecular weight of 366 and a specific rotatory power $[\alpha]_D$ of $+115°$, and presents an NMR spectrum described below:

H-NMR/$D_2O$ 3.3 (ppm), dd, 1H, 3.5 (ppm), m, 1H, 3.5 (ppm), t, 1H, 3.6 (ppm), d, 1H, 3.6 (ppm), d, 1H, 3.7 (ppm), d, 1H, 3.7 (ppm), d, 1H, 3.8 (ppm), ddd, 1H, 4.1 (ppm), dd, 1H, 4.2 (ppm), d, 1H, 4.8 (ppm), ddd, 1H, 5.2 (ppm), d, 1H, $^{13}$C-NMR/$D_2O$: 63.5 (ppm), 64.8 (ppm), 72.4 (ppm), 72.8 (ppm), 74.8 (ppm), 75.8 (ppm), 76.2 (ppm), 83.0 (ppm), 83.2 (ppm), 83.4 (ppm), 85.6 (ppm), 89.9 (ppm), 163.8 (ppm), to a process for preparing said substance, and to actinomycetes capable of producing said substance.

Trehalostatin of the present invention shows an inhibitory effect against trehalase in insects, especially *Aldrichina grahami*, even at a very low concentration and is therefore useful as an insecticide.

1 Claim, No Drawings

AMYCOLATOPSIS TREHALOSTATICA STRAIN

TECHNICAL FIELD

The present invention relates to a substance Trehalostatin. The invention also relates to a process for the preparation of said substance Trehalostatin and actinomycetes which produce said substance.

BACKGROUND ART

Trehalase is one of the glucohydrolases. It is an enzyme which catalyzes hydrolysis of the α-glucosidic linkage of trehalase which is widely distributed in mold, yeast and hemolymph of many species of insects.

DISCLOSURE OF THE INVENTION

The present inventors found that the actinomycetes belonging to the genus Amycolatopsis, which had been separated from soil, can yield a substance which shows an inhibitory effect against trehalase in insects, especially in *Aldrichina grahami*, at a very low concentration. This substance was named Trehalostatin.

The present invention was accomplished on the basis of said finding, and it relates to the substance Trehalostatin which has been collected from the cultures of a trehalostatin-producing actinomycete belonging to the genus Amycolatopsis. The present invention also provides actinomycetes strains which can yield such a novel substance and a process for the preparation of Trehalostatin by using said strains.

The actinomycete usable in the present invention include all of those belonging to the genus Amycolatopsis, a typical example of which is *Amycolatopsis trehalostatica*, and capable of yielding Trehalostatin.

Especially the strain SAM 0967 which was newly separated from soil by the present inventors can be used most preferably.

*Amycolatopsis trehalostatica* SAM 0967 has the following taxonomical properties.

1. Morphological characteristics

The substrate and aerial mycelium are formed and measure 0.4–0.8 μm in diameter. The substrate mycelium is branched and exhibits occasional fragmentation. The aerial mycelium is also branched and formed spore chain with 10 or more spore per chain. Each spore measures 0.4 to 0.5 μm in width and 0.9 to 1.3 μm in length and has a smooth surface. No sporangia, synnemata, or sclerotia were observed even after 21 days of cultivation.

2. Cultural characteristics

Sucrose-nitrate agar: aerial mycelium are abundant and white; brownish orange in reverse; soluble pigment is grayish purple.

Glucose-asparagine agar: aerial mycelium are abundant and white; grayish orange in reverse; no soluble pigment.

Glycerol-asparagine agar: aerial mycelium are abundant and white; grayish brown in reverse; soluble pigment is grayish orange.

Starch-inorganic acid agar: aerial mycelium are abundant and white; whitish yellow in reverse; no soluble pigment.

Tyrosine agar: aerial mycelium are abundant and white; dark brown in reverse; soluble pigment is grayish brown.

Nutrient agar; aerial mycelium are abundant and white; whitish yellow in reverse; no soluble pigment.

Yeast extract-malt extract agar: aerial mycelium are abundant and white; dark brown in reverse; soluble pigment is grayish brown.

Oatmeal agar: aerial mycelium are abundant and white; whitish yellow in reverse; no soluble pigment.

1/10 potato-carrot agar: aerial mycelium are abundant and white; whitish yellow in reverse; no soluble pigment.

1/10 V-8 juice agar: aerial mycelium are abundant and white; whitish yellow in reverse; no soluble pigment.

3. Physiological characteristics (1) Growth temperature

As a result of culture tests conducted at temperature of 16° C., 19° C., 22° C., 25.5° C., 28.5° C., 31° C., 33° C., 36.5° C., 39.5° C., 42.5° C., 45.5° C. and 47° by using Yeast extract-glucose broth, the temperature range for growth was 19–39.5° C., with optimum growth occurring at 28.5–36.4° C.

(2) Gelatin liquefaction (28°)

Glucose-peptone-gelatin medium: positive Simple gelatin medium: positive Meat extract-gelatin medium: positive (3) Hydrolysis of starch: positive (4) Coagulation of skim milk (28°): negative (5) Peptonization of skim milk: positive (6) Formation of melanin-like pigment Peptone-yeast extract iron agar: negative Tyrosine agar: negative Triptone-yeast extract agar: negative (7) Reduction of nitrate: positive (8) Utilization of carbohydrates (tested on Pridham and Gottlieb carbon utilization medium at 28° C. for 14 days)

D-glucose: +
D-xylose: +
L-lactose: +
L-rhamnose: +
L-arabinose: +
D-fructose: +
Raffinose: ±
D-mannitol: +
Inositol: +
Sucrose: +
Lactose: +

(notes) +: utilized; ±: doubtful; −: not utilized (9) Acid production from carbohydrates Raffinose: +
Inositol: +
Lactose: +
Sorbitol: −
Erythritol: −
L-arabinose: +
Adonitol: −
D-galactose: +

As determined by the method described by R.E. Gordon et al., *Internal Journal of Systematic Bacteriology*, Vol. 24, p. 54, (1974).

4. Chemotaxonomy (1) 2,6-diaminopimelic acid

The presence of meso-2,6-diamnopimelic acid was detected as a result of examination of the hydrolyzate of the whole cell and its cell wall according to the method described by J.L. Staneck and G.D. Roberts, *Applied Microbiology*, Vol. 28, p. 226, (1974)

(2) Sugars

The presence of arabinose was detected in the hydrolyzate of the whole cell. There was also admitted the presence of galactose and arabinose in the hydrolyzate of the cell wall.

(3) Menaquinones

MK-9 (H4) is the major menaquinone components.

on yeast extract malt extract agar and inorganic salts-starch agar, growth in the presence of 5% NaCl, utilization of sucrose, acid production from raffinose, erythritol and adonitol, and menaquinone composition.

In addition, strain SAM 0967 is clearly distinguished from *Amycolatopsis mediterranei* by the formation of aerial mycelium and menaquinone composition.

TABLE

Distinguishing taxonomical properties of *Amycolatopsis trehalostatica*, *Amycolatopsis orientalis* and *Amycolatopsis mediterranei*.

| taxonomical properties | A. trehalostatica ASM 967$^T$ | A. orientalis JCM 4600$^T$ | A. mediterranei JCM 4789$^T$ |
|---|---|---|---|
| Formation of Aerial mycelium | + | + | —* |
| Color of Aerial mycelium | | | |
| Yeast extract-malt extract agar | White | White (Blue***) | — |
| Inorganic salts - Starch agar | White | White (Blue***) | — |
| Growth in the presense of 5% NaCl | — | + | — |
| Utilization of carbohydrates | + | — | + |
| Sucrose | | | |
| Acid produced from: | | | |
| Raffinose | + | — | + |
| Erythritol | — | + | — |
| Adonitol | — | + | — |
| Menaquinone composition** | | | |
| MK-9 | — | + | — |
| MK-9 (H2) | — | ++ | +++ |
| MK-9 (H4) | +++ | +++ | +++ |

$^T$Type strain
*Scant aerial mycelium was produced only on Pridham and Gottlieb carbon utilization medium.
**The compositional ratio of menaquinone components are —: <5%; +: 5-14; ++: 15-49%; +++: >50%.
***Blue aerial mycelium was produced on the outside edge of colony.

(4) Phospholipid type

The present actinomycete strain contains phosphatidyl ethanolamine and doe sot contain phosphatidyl chlorine and an unknown glycosamine-containing phospholipid. This falls under type P II phospholipid pattern according to .P. Lechevalier and H.A. Lechevalier, "The Chemotaxonomy of Actinomycetes," pp. 227-291, in *Actinomycete Taxonomy*, Special Publication No. 6, Society for Industrial Microbiology (edited by A. Dietz and D.W. Thayer), U.S.A., 1980.

(5) Mycolic acid

No mycolic acid was detected in the cell.

Strain SAM 0967 has a type IV cell wall composition (meso-2,6-diaminopimelic acid, galactose and arabinose as diagnostic constituents) and a type A whole-cell sugar pattern (arabinose and galactose). Strain SAM 0967 produces the aerial mycelium forming spore chain with 10 or more smooth-surface spores per chain at the end of each aerial mycelium. The major menaquinone component of strain SAM 0967 is of then MK-9 (H4). Its phospholipid type is P-II. No mycolic acid is detected.

From the above taxonomical properties, strain SAM 0967 can be identified as an actinomycete belonging to the genus *Amycolatopsis*. At present, 6 species and 1 subspecies are assigned to the genus *Amycolatopsis*.

See, M.P. Lechevalier et al., *International Journal of Systematic Bacteriology*, Vol. 36, p. 29, (1986) and A. Henssen et al., *International Journal of Systematic Bacteriology*, Vol. 37, p. 292, (1987), SAM 0967 resembles *Amycolatopsis orientalis* and *Amycolatopsis mediterranei*. Thus, the present inventors made a comparison of taxonomic properties between strain SAM 0967 and the strains, *Amycolatopsis orientalis* and *Amycolatopsis mediterranei*.

As seen in the following table, strain SAM 0967 is clearly distinguished from *Amycolatopsis orientalis* by several indicia, including, the color of aerial mycelium The present inventors believe that the differences provides above are enough to taxonomically distinguish strain SAM 0967 from said two species; thus the present inventors have concluded that strain SAM 0967 represents a new species within the genus *Amycolatopsis*. Therefore, the present inventors have designated strain SAM 0967 as *Amycolatopsis trehalostatica*.

*Amycolatopsis trehalostatica* SAM 0967 was deposited under accession number FERM P-10544 at the Fermentation Research Institute of Agency of Industrial Science and Technology at the date of Feb. 17, 1989,a nd later it was transferred, on Feb. 28, 1990, to international deposition made under the requirements of the Budapest Treaty on the International Recognition of the Deposit of Microorganisms for the Purpose of Patent procedure, from which it is available under accession number FERM BP-2784.

In the present invention, the actinomyces such as described above are cultured. A medium used for the cultivation may be either liquid or solid, but usually shaking culture or aerated spinner culture in a liquid medium is expedient.

It is possible to use any type of medium as far as it enables growth of the actinomyces according to the present invention and is capable of accumulating the novel substance of this invention. As carbon source, for instance, there may be used glucose, lactose, starch, sucrose, dextrin, molasses, organic acids, etc. As nitrogen source, there may be used protein hydrolyzates such as peptone and Casamino acid, meat extract, yeast extract, soybean cake, corn steep liquor, amino acids, ammonium salts, nitrates and other organic or inorganic nitrogen compounds. Various types of phosphates, magnesium sulfate, sodium chloride and the like may be added as an inorganic salt. Also, vitamins, nucleic acid-associated compounds and such may be added for the purpose of promoting growth of the actinomycete. In some cases, it is effective for promoting accumulation amount of the novel substance of this invention to add a defoaming agent such as silicon, polypropylene glycol derivatives, soybean oil and the like in the medium.

In carrying out the cultivation in the present invention, it is desirable to initially perform a small-scale pre-cultivation and to inoculate the resulting culture into a medium to conduct the primary cultivation. In both preliminary and primary cultivation, the culturing conditions such as cultivation temperature, cultivation period and properties of the culture medium are properly selected and adjusted so as to maximize the amount of the novel substance of this invention accumulated in the medium. In many cases, the cultivation is preferably carried out under an aerobic condition at a temperature of 25-30° C. In case of using a liquid medium, it is recommended to maintain pH of the medium at 5.5-8.0. In the course of such cultivation, the substance of the present invention is produced and accumulated in the culture. When cultivation is carried out by using the liquid medium, the objective substance is accumulated principally in a liquid phase portion of the medium, so that it is desirable to filter or centrifuge the cultures to remove the cells and then to separate the objective substance from the filtrate or supernatant. In certain cases, however, the objective substance may be directly separated from the liquid culture without removing the cells from them.

The detection and determination of the substance Trehalostatin of this invention during the separation and collection can be accomplished by determining the degree to which said substance can inhibit an activity of trehalase extracted from *Aldrichina grahami* or porcine kidney. For the separation and purification of the objective substance from the cultures, there can be employed various means in accordance with chemical characteristics of the substance of this invention. For instance, it is effective to employ treatment with an organic solvent, gel filtration by Sephadex or Biogel, ion exchange chromatography using various types of ion exchange resin, adsorption chromatography using an absorbent such as activated carbon, silica gel and Amberlite XAD-1 or XAD-2 and normal-phase chromatography using a carrier such as YMC-PA 43 or TSK-Amide 80. By using these means in a proper combination, the novel substance Trehalostatin of this invention can be isolated as white amorphous powder. Other methods than those mentioned above may also be used as far as such methods can effectively utilize the characteristics of the novel substance of this invention. An especially preferred combination the absorbent is that of Dowex 50WX4 (H), YMC-PA43 and TSK-Amide 80.

The substance of this invention can be used after its isolation and purification, but in some cases, the culture of the Trehalostatin-producing actinomycete can be used in the form as it is or only after a simple purification.

BEST MODE FOR CARRYING OUT THE INVENTION

The present invention will be described in detail below by showing the examples thereof, but the present invention is not limited to these examples.

EXAMPLE 1

Preparation of Trehalostatin (1) Activity determination method

The inhibitory activity of Trehalostatin in each stage of its purification was determined in the following way.

10 $\mu$l of an inhibitor solution and 10 $\mu$l of a trehalase solution (trehalase collected from *Aldrichina grahami*) were mixed. After 5-minute incubation at 37° C, 80 $\mu$l of a 5 mM trehalose and 50 mM phosphate buffer solution (pH6.5) was added, followed by an additional one-hour incubation at 37° C. Thereafter, 10 $\mu$l of a 50% trichloroacetic acid solution was added to terminate the reaction. Glucose formed in the reaction solution was determined by a new blood sugar test manufactured by Boehringer-Mannheim Ltd. The amount of the enzyme was such that absorbance of the wavelength (660 mm) used in the glucose determination when conducted according to the above method without adding the inhibitor would become 1.0. The Trehalostatin concentration which can achieve 50% inhibition of enzyme (trehalase) activity in the above determination method was expressed as 1 unit/ml.

(2) Preparation of Trehalostatin by cultivation of

*Amycolatopsis trehalostatica*

30 ml of pure culture of SAM 0967 strain was inoculated into 3 1 liters of a medium (pH 7.0) composed of hot water extract of potato, glucose, dry yeast extract, potassium monophosphate and magnesium sulfate and cultivated in a 5-liter jar fermenter at 28° C. × for 120 hours (aeration, 1 vvm; agitation, 400 rpm).

To 3.07 liters of supernatant (containing 101,000 units of Trehalostatin) obtained by centrifugation of the culture, formic acid- was added to a final concentration of 0.02 M. After adjusting pH of the solution to 3.1 with hydrochloric acid, the solution was applied to a column (6×37 cm) of Dowex 50W × 4 (H) (mfd. by Muromachi Chemical Co., Ltd.). This column was washed with 3.0 liters of 0.2 M pyridineformic acid buffer (pH 3.2) and the substance having the activity inhibiting trehalase of *Aldrichina grahami* was eluted in 3.5 liters of 0.4M pyridine-acetic acid buffer (pH 4.2).

The active fraction (containing 120,000 units of Trehalostatin) was concentrated and evaporated to dryness under reduced pressure, and the residue was dissolved in a small quantity of water and pH of the solution was adjusted to 3.1 with hydrochloric acid. The insolubles in the solution were removed by centrifuge, and the resultant supernatant was passed through a column (3×12 cm) of Dowex 50W × 4 (H) This column was washed with 0.5 liter of deionized and then further washed with 3 liters of 0.2 M pyridine-formic acid buffer (pH 3.2) containing 30% (v/v) of methanol to elute the objective substance.

The fraction of the objective substance (containing 20,000 units of Trehalostatin) was concentrated under reduced pressure. The residue was uniformly suspended in 50% (v/v) acetonitrile and charged into a packed column for high-performance liquid chromatography (YMC-PA 43, 2.5×7 cm). This column was washed with a 65% (v/v) acetonitrile solution of a determined composition (flow rate: 5 ml/min), and the eluate was fractionated in portions of 5.0 ml and detected by a differential refractometer. As a result, the fraction having trehalase-inhibiting activity (containing 19,000 units of Trehalostatin) was eluted at around 200 ml after the charging.

The fraction containing the objective substance was concentrated, dissolved in 40% (v/v) acetonitrile and charged into a packed column for high-performance liquid chromatography (TSK-Amide 80, 0.7×27 cm). This column was washed with a solvent of the same composition (flow rate: 1 ml/min) and the eluate was fractionated in portions of 0.5 ml and detected by a differential refractometer. The fraction having trehalase-inhibiting activity was eluted at around 25–30 ml after the charging. The fraction of the objective substance (containing 118,000 units of Trehalostatin) was evaporated to dryness, added with water and then freeze-dried, thereby obtaining 1 mg of a pure objective substance.

EXAMPLE 2

Physicochemical properties of Tehalostatin

The substance separated from the culture of *Amycolatopis trehalostatica (SAM 0967)* and purified according to Example 1 was named Trehalostatin.

The physical and chemical properties of this Trehalostatin are shown below.

Appearance: white powder
Solubility: soluble in water but hardly or only slightly soluble in hexane, benzene, ethers and petroleum ether
Ultraviolet and visible light absorption spectrum: having no absorption maxima at 220 nm or above
Color reaction: positive in Rydon-Smith reaction and negative in ninhydrin reaction, 3,6-dinitrophthalic acid reaction and Elson-Morgan reaction
Thin-layer chromatography: Rf=0.37 (Merck Kieselgel 60 $F_{254}$, developing solvent: 3:1:2 mixture of n-butanol, acetic acid and water)
High-performance liquid chromatography: Rt=11.0 min. (column: YMC PA03, 0.7×27 cm; solvent: 65% v/v acetonitrile in H2O; flow rate: 1.0 ml/min; detection: deferential refractomer)
Molecular weight: 366 (m/z 367, M+H, SIMS)
$[\alpha]_D$: +115°
$1_{H-NMR/D2O}$: 3.3 (ppm), dd, 1H,
3.5 (ppm), m, 1H,
3.5 (ppm), t, 1H,
3.6 (ppm), d, 1H,
3.6 (ppm), d, 1H,
3.7 (ppm), d, 1H,
3.7 (ppm), d, 1H,
3.8 (ppm)liter, dddliter, 1H,
4.1 (ppm), dd, 1H,
4.2 (ppm), d, 1H,
4.8 (ppm), ddd, 1H,
5 2 liter(ppm), d, 1H,
$13_{C-NMR/D2O}$: 63.5 (ppm),
64.8 (ppm),
72.4 (ppm),
72.8 (ppm),
74.8 (ppm),
75.8 (ppm),
76.2 (ppm),
83.0 (ppm),
83.2 (ppm),
83.4 (ppm),
85.6 (ppm),
89.9 (ppm),
163.8 (ppm), A structural formula of the present substance that can be assumed from the above results is such as shown below as Formula 1 or Formula 2:

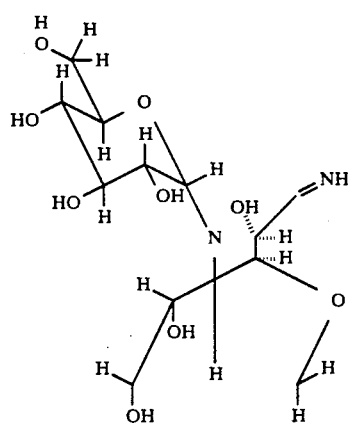

Formula 1

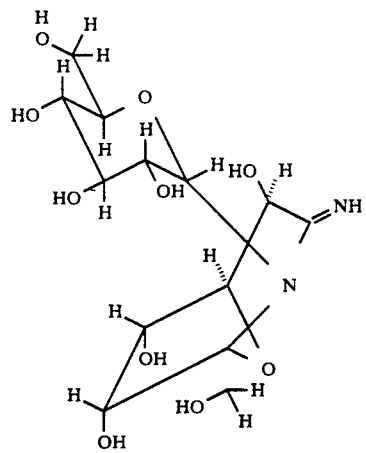

Formula 2

EXAMPLE 3

Enzyme inhibition spectrum of Trehalostatin

| Enzyme | Origin | Amount of enzyme (μg) | Reacting conditions | Activity measuring method | Action |
| --- | --- | --- | --- | --- | --- |
| Trehalase | (*Aldrichina grahami*)[4] | 24* | pH 5.5, 5 mM trehalase | A | ++ |
| | (*Chaetomium aureum*)[4] | 15 | pH 5.5, 5 mM trehalase | A | + |
| | (bovine colonic mucosa)[1] | 2500 | pH 5.5, 5 mM trehalase | A | + |
| | (swine kideny)[2] | 1.1* | pH 6.5, 5 mM trehalase | A | + |
| α-glycosidase | (yeast)[3] | 1 | pH 7.1, 5 mM | A | + |

-continued

| Enzyme | Origin | Amount of enzyme (μg) | Reacting conditions | Activity measuring method | Action |
|---|---|---|---|---|---|
| β-glycosidase | (Asp. aculeatus)[4] | 15 | P-nitrophenyl glycoside pH 5.0, 0.5% salicin | A | + |
| Gluco amylase | (almond)[5] | 10 | pH 5.0, 0.5% salicin | A | − |
|  | (Rhizopus niveus) | 2 | pH 5.5, 0.5% starch | A | − |
| exo-β-1,3-glucanase |  | 15 | pH 6.0, 0.1% laminarin | B | − |
| avicelase | (Asp. aculeatus)[4] | 2000 | pH 5.0, 0.5% avicel | C | − |
| Bacterial saccharifying amylase |  | 4 | pH 5.0, 0.5% starch | C | − |
| Bacterial liquefying amylase |  | 0.4 | pH 5.0, 0.5% starch | C | − |
| β-amylase | (sweet potato)[5] | 12.5 | " | C | − |
| Invertase | (bovine colonic mucosa)[1] | 5000 | pH 6.0, 0.1% sucrose | A | − |
| Taka-amylase A[9] | (yeast)[8] | 100 | pH 5.5, 0.1% sucrose | A | − |
|  |  | 0.5 | pH 5.5, 0.5% starch | 69 | − |
| Carboxymethyl-cellulase | (Asp. aculeatus)[4] | 100 | pH 5.0, 0.5% CM cellulose | C | − |
| Isoamylase[10] |  | 100 | pH 5.5, 0.5% starch | C | − |

++: $ID_{50} \leq 1.0$ μg
+: $ID_{50} \geq 1.0$ μg
−: no inhibition
*unit (nmol glucose/min)
(Notes)
[1] mucosal acetone powder Sigma (M-2766)
[2] Sigma (M-8778)
[3] produced by TOYOBO. Co., Ltd.
[4] a crude enzyme (prepared by University of Osaka Prefecture)
[5] Sigma
[6] produced by Seikagaku Kogyo Co., Ltd.
[7] produced by Daiwa Kasei Co., Ltd.
[8] Wako Pure Chemicals Co., Ltd.
[9] SANKYO Co., Ltd.
[10] Shin Nippon Kagaku Co., Ltd.

Method

Each enzyme (200 μl) is incubated with Trehalostatin (0.01–50 μg) in 0.05M acetate (pH 5–6) or phosphate (pH 6–7) buffer solution at 37° C. for 5 minutes. Then 20 μl of the resulting solution is collected and added with a substrate to a final concentration shown in the Table, making the total volume of the solution 100 μl. The mixture is incubated at 37° C. for 10 minutes and then incubated in a boiling water bath for 3 minutes to terminate the reaction.

Determination of activity was made by measuring the increase of the product in the reaction system according to the following methods A-C.

The quantity of Trehalostatin which can effect 50% inhibition of enzyme activity under the above-described conditions was indicated as $ID_{50}$.

(A) The glucose produced was determined by the new blood sugar test deviced by Boehringer-Mannheim Ltd..

(B) An amount of glucose produced was determined according to the method shown in D.R. Barras and B.A. Stone: Biochim. Biophys. Acta 191, 329, 1969.

(C) The increase of an amount of reducing sugar produced was measured according to the method shown in J.A. Thoma et al: The Enzyme (3rd. ed.) 5, 115–189, 1971.

Industrial Applicability

Trehalostatin of the present invention exhibits an effective inhibitory effect against trehalase in insects, especially in *Aldrichina grahami*, even at a very low concentration and is thus useful as an insecticide for these insects.

We claim:

1. An isolated and substantially biologically pure culture of *Amycolatopis trehalostatica* SAM 0967, having the identifying characteristics of which shows an inhibitory effect against trehalase in insects.

* * * * *

UNITED STATES PATENT AND TRADEMARK OFFICE
CERTIFICATE OF CORRECTION

PATENT NO. : 5,169,778
DATED : December 8, 1992
INVENTOR(S) : Murao et al.

It is certified that error appears in the above-identified patent and that said Letters Patent is hereby corrected as shown below:

On the title page, Item [30]: change priority date to read
--February 28, 1989--

Signed and Sealed this

Twenty-eighth Day of December, 1993

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,169,778
DATED : December 8, 1992
INVENTOR(S) : Murao et al

It is certified that error appears in the above-indentified patent and that said Letters Patent is hereby corrected as shown below:

On the title page: Item [73] change name of Assignee from "Sawao Murao, Osaka, Japan" to --Suntory Limited, Osaka, Japan --.

Signed and Sealed this

Thirty-first Day of January, 1995

Attest:

BRUCE LEHMAN

*Attesting Officer*      *Commissioner of Patents and Trademarks*